US011195602B2

(12) United States Patent
Myers et al.

(10) Patent No.: US 11,195,602 B2
(45) Date of Patent: Dec. 7, 2021

(54) SYSTEM AND METHOD TO ELECTRONICALLY COORDINATE AND DOCUMENT PATIENT CARE REGARDLESS OF PHYSICAL SETTING

(71) Applicant: Vivonics, Inc., Bedford, MA (US)

(72) Inventors: Ryan Myers, North Andover, MA (US); Gordon B. Hirschman, Cohoes, NY (US)

(73) Assignee: Vivonics, Inc., Bedford, MA (US)

( * ) Notice: Subject to any disclaimer, the term of this patent is extended or adjusted under 35 U.S.C. 154(b) by 0 days.

(21) Appl. No.: 16/887,180

(22) Filed: May 29, 2020

(65) Prior Publication Data

US 2020/0381094 A1 Dec. 3, 2020

Related U.S. Application Data

(60) Provisional application No. 62/855,267, filed on May 31, 2019.

(51) Int. Cl.
*G16H 10/65* (2018.01)
*H04W 4/80* (2018.01)
(Continued)

(52) U.S. Cl.
CPC .......... *G16H 10/65* (2018.01); *A61B 5/6833* (2013.01); *G06F 1/163* (2013.01); *H04W 4/80* (2018.02)

(58) Field of Classification Search
CPC ......... G06F 1/163; A61B 5/6833; H04W 4/80
See application file for complete search history.

(56) References Cited

U.S. PATENT DOCUMENTS

2011/0172550 A1* 7/2011 Martin .................. G06Q 50/24
600/523
2011/0175735 A1* 7/2011 Forster ................. A61B 5/6833
340/573.1
(Continued)

FOREIGN PATENT DOCUMENTS

KR 20150066560 A * 6/2015 ............. G01K 1/024

OTHER PUBLICATIONS

Haahr, Rasmus G. "An Electronic Patch for Wearable Health Monitoring by Reflectance Pulse Oximetry." IEEE Transactions on Biomedical Circuits and Systems, vol. 6, No. 1, Feb. 2012 (Year: 2012).*

(Continued)

*Primary Examiner* — Linh Giang Le
(74) *Attorney, Agent, or Firm* — Iandiorio Teska & Coleman, LLP

(57) ABSTRACT

A system to electronically coordinate and document patient care regardless of physical setting. The system includes a wearable subsystem attached to a patient at the point of injury and configured to remain attached to the patient at the point of injury and during one or more encounters with medical personnel or to a time the patient reaches a clinical health care facility. The wearable subsystem is configured to store patient identification information and critical health care information received via wireless communication from an end user computing device at the point of injury and is configured to store added health care information provided by medical personnel from or at the point of injury and during the one or more encounters with the medical personnel or to a time the patient reaches a clinical care facility.

28 Claims, 9 Drawing Sheets

(51) Int. Cl.
  *G06F 1/16*       (2006.01)
  *A61B 5/00*       (2006.01)

(56) References Cited

U.S. PATENT DOCUMENTS

| | | | | |
|---|---|---|---|---|
| 2012/0255875 A1* | 10/2012 | Vicente | .................. | G16H 40/67 |
| | | | | 205/782 |
| 2014/0121557 A1* | 5/2014 | Gannon | .................. | A61B 5/002 |
| | | | | 600/549 |
| 2014/0154656 A1* | 6/2014 | Segall | .................. | G09B 23/285 |
| | | | | 434/265 |
| 2014/0230819 A1* | 8/2014 | Rawlins | ............... | A61B 5/0022 |
| | | | | 128/204.23 |

OTHER PUBLICATIONS

Butler, F.K. et al., Tactical Combat Casualty Care in Special Operations, Military Medicine, vol. 16 1, Supplement 1, 1996, 15 pages.

Butler, Frank K., Tactical Combat Casualty Care: Update 2009, Th Journal of Trauma® Injury, Infection, and Critical Care, vol. 69, No. 1, July Supplement 2010.

Eastridge, Brian J. et al., Death on the Battlefield (2001-2011): Implications For the Future of Combat Casualty Care, Trauma Acute Care Surg., vol. 73, No. 6, supplement 5, 2012, 7 pages.

Stahl, Kenneth et al., Enhancing Patient Safety in the Trauma/Surgical Intensive Care Unit, The Journal of Trauma® Injury, Infection, and Critical Care, vol. 67, No. 3, Sep. 2009, pp. 430-435.

\* cited by examiner

SYSTEM AND METHOD TO ELECTRONICALLY COORDINATE AND DOCUMENT PATIENT CARE REGARDLESS OF PHYSICAL SETTING

RELATED APPLICATIONS

This application claims benefit of and priority to U.S. Provisional Application Ser. No. 62/855,267 filed May 31, 2019, under 35 U.S.C. §§ 119, 120, 363, 365, and 37 C.F.R. § 1.55 and § 1.78, which is incorporated herein by this reference.

GOVERNMENT RIGHTS

This invention was made in part with U.S. Government support under Contract No. W81XWH-18-C-0134, awarded by the U.S. Army Medical Research Acquisition Activity. The Government has certain rights in the invention.

FIELD OF THE INVENTION

This invention relates to a system and method to electronically coordinate and document patient care regardless of physical setting.

BACKGROUND OF THE INVENTION

The "golden hour" is a well-studied and documented period after the onset of out-of-hospital traumatic injury wherein the chance of morbidity increases the longer a patient is not properly cared for. Nearly 90% of combat casualty fatalities occur prior to reaching a properly equipped medical center, with nearly a quarter of the 4,596 combat deaths in Iraq and Afghanistan between 2001 and 2011 classified as 'potentially survivable' See e.g., Eastridge, B. J., et al., *Death on the battlefield* (2001-2011): *Implications for the Future of Combat Casualty Care*, Journal of Trauma and Acute Care Surgery, 73(6), pp. S431-S437 (2012), incorporated by reference herein. To address these long-standing point-of-injury trauma care issues within the battlefield, Butler, et al. developed a novel prehospital trauma management approach known as Tactical Combat Casualty Care (TCCC). TCCC has saved countless military and civilian lives by normalizing, priority driven care. See e.g. Butler, F. K., J. Haymann, and E. G. Butler, *Tactical Combat Casualty Care in Special Operations*, Association of Military Surgeons of the U.S., 161(suppl_1), pp. 3-16, (1996), incorporated by reference herein. The documentation of the care delivered via this approach, currently performed by the U.S. Military on a paper TCCC Card (DD Form 1380), is imperative not only to communicate patient status, injury, and treatments to subsequent providers, but also to allow those monitoring the TCCC approach to evaluate its efficacy in a quantitative manner. Unfortunately, less than 10% of the 30,000 casualties in Iraq and Afghanistan had any form of documentation of their combat casualty care in their medical records, substantially hindering the aforementioned processes, and leading to a staggering 67% of sentinel events being attributed to an error in communication. See e.g. Butler, F. K., *Tactical Combat Casualty Care: Update* 2009, Journal of Trauma and Acute Can Surgery, 69(1), pp. S10-S13 (2010) and Stahl, K., et al, *Enhancing Patient Safety in the Trauma/Surgical Intensive Care Unit*, Journal of Trauma and Acute Care Surgery, 67(3), p. 430-435 (2009), both incorporated by reference herein. Identifying this gap in care coordination, the military and civilian emergency medical services have gone to great lengths to improve their electronic record keeping capabilities, resulting in an electronic version of the TCCC card that can and is being implemented into end user computing devices, e.g., the Army's NETT Warrior, the Air Forces BATDOK, and SOCOM's ATAK, as well as into civilian EMS electronic medical record systems. However, to date there is no known system or method to electronically coordinate and document patient care regardless of physical setting.

SUMMARY OF THE INVENTION

In one aspect, a system to electronically coordinate and document patient care regardless of physical setting is featured. The system includes a wearable subsystem attached to a patient at the point of injury and configured to remain attached to the patient at the point of injury and during one or more encounters with medical personnel or to a time the patient reaches a clinical health care facility. The wearable subsystem is configured to store patient identification information and critical health care information received via wireless communication from an end user computing device at the point of injury and is configured to store added health care information provided by medical personnel from or at the point of injury and during the one or more encounters with the medical personnel or to a time the patient reaches a clinical care facility.

In one embodiment, the wearable subsystem may be configured as an adhesive patch. The adhesive patch may include a flexible printed circuit board. The flexible printed circuit board may include one or more of a processing subsystem, an electronic storage device, firmware, and a power supply. The adhesive patch may include a plurality of flexible layers about the flexible printed board. One of the plurality of flexible layers may include an adhesive layer configured to attach to the skin of the patient. One or more of the plurality of flexible layers may be configured to increase moisture vapor transmission rate of vapor from skin of the patient to provide increased breathability and attachability of the adhesive patch subsystem to the skin. The flexible printed circuit board may include a breathable substrate configured to increase moisture vapor transmission rate of vapor from skin of the patient to provide increased breathability. The flexible printed circuit board may include a plurality of openings configured to increase moisture vapor transmission rate of vapor from skin of the patient to provide increased breathability. The wearable subsystem may have a small area. The area of the wearable subsystem may be less than about 35 cm$^2$. The power supply may include a small sized battery configured to provide power for an extended period of time. The power supply may include a supercapacitor configured to provide power for an extended period of time. The wearable subsystem may be attached to an easily accessible area of the patient. The wearable subsystem may be configured to transfer the patient identification information and critical health care information and the health care information added by the medical personnel to an electronic medical record or electronic health record. The wearable subsystem may be configured to operate regardless of a state of long distance communication. The wearable subsystem may be configured to operate using short range communication. The end user computing device may be configured to capture via wireless communication the patient identification information and the critical health care information from an electronic personal identification device already located on a patient at a point of injury. The end user computing device may operate using short range communication. The end user computing device may include one or more casualty care programs configured to input and/or receive and store the patient identification information and critical health care information and the health care information provided by the medical personnel. The one or more casualty care programs may include an electronic Tactical Combat Casualty Care Program (TCCC). The one or more casualty care programs may include an electronic Patient Care Reporting (ePCR) subsystem.

In another aspect, a method for electronically coordinating and documenting patient care regardless of physical setting is featured. The method includes attaching a wearable subsystem to a patient at a point of injury, the wearable subsystem configured to remain attached to the patient at the point of injury and during one or more encounters with medical personnel or to a time the patient reaches a clinical care facility and storing patient identification information and critical care health care information received via wireless communication from an end user computing device at the point of injury on the wearable subsystem and storing added healthcare information provided by the medical personnel from or at the point of injury and during one or more encounters with medical personnel or to a time the patient reaches the clinical care facility.

In one embodiment, the wireless communication may include short range communication. The method may further include transferring the patient identification information and critical health care information and health care added by medical personnel to an electronic medical record or an electronic health record. The method may further include increasing moisture transmission rate of the wearable subsystem to provide increased breathability and attachability of the wearable subsystem to the patient. The method may further include capturing via wireless communication the patient identification information and critical health care information from an electronic personal communication device already located on the patient at the point of injury. The method may further include capturing via the patient identification information and critical health care information from an electronic personal communication device already located on the patient at the point of injury using short range communication.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
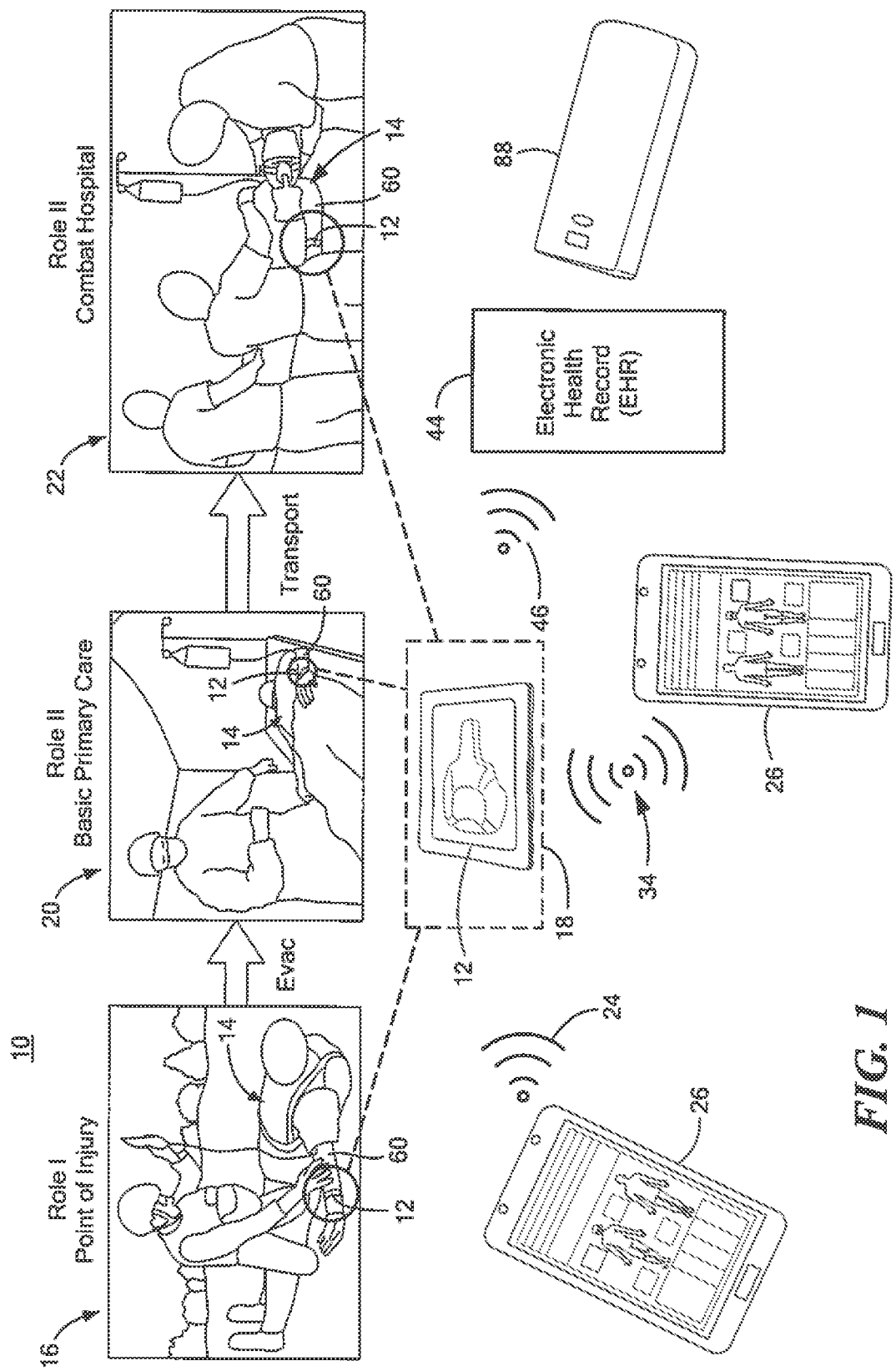
FIG. 1 is a schematic block diagram showing the primary components of one embodiment of the system and method to electronically coordinate and document patient care regardless of physical setting.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

There is shown in FIG. 1 one example of system 10 to electronically coordinate and document patient care regardless of physical setting. System 10 includes wearable subsystem 12, shown in greater detail in caption 18, attached to patient 14 at point of injury 16. Patient 14 may be an armed forces soldier or other military personnel injured at point of injury 16 in a combat situation or a civilian injured at a point of injury. Wearable subsystem 12 remains attached to patient 14 from point of injury 16 and during one or more encounters of patient 14 with medical personnel or to a time patient 14 reaches a clinical hospital facility, e.g., combat hospital 22 or similar type clinical care facility. The medical care provided to patient 14 by medical personal may be at point of injury 16 and/or during the one or more encounters with medical personnel, e.g., during basic primary care 20 which may include, inter alia, interventions for broken bones, medications administered, field intubation, or any other medical procedure, intervention, and the like, provided to patient 14 by medical personnel.

Wearable subsystem 12 is preferably easily maintained through multiple patient handoffs, e.g., from point of injury 16, evac to basic primary care 20, and transport to clinical care facility 22. Because a conventional patch is often used by medical personnel and non-medical personnel, little training is required for applying wearable subsystem 12 to an injured patient, as discussed below.

Wearable subsystem 12 stores patient identification information and critical healthcare information received via wireless communication, indicated at 24, from end user computing device 26 at point of injury 16, as discussed in detail below. Wearable subsystem 12 also stores healthcare information added by medical personnel to end user computing device 26 from or at point of injury 16 and during one or more encounters with medical personnel received via wireless communication, indicated at 34, from end user computing device 26.

Wearable subsystem 12 of system 10 may also be referred to herein as Persistent Access to Tactical Casualty Health (PATCH) subsystem 12. Wearable or PATCH subsystem 12 is preferably a high capacity device that is designed for efficient and rapid two-way communication between the end user computing device 26 and wearable or PATCH subsystem 12. The health care information regarding care provided to patient 14 may be altered, amended, and/or added to by end user computing device 26 to include care provided to patient 14 during or at point of injury 16 and/or during one or more encounter with medical personnel. The updated information regarding the care provided to patient 14 is preferably transferred, or downloaded, via wireless communication from end user computing device 26 to wearable or PATCH subsystem 12.

End user computing device 26 is preferably a smart device, e.g., a smartphone, a cellular phone, a tablet, a PDA, or similar type smart device that includes one or more processors, an electronic storage device or memory, and preferably includes one or more casualty care programs, e.g., an electronic Tactical Combat Casualty Care Program (TCCC), electronic Patient Care Reporting (ePCR) subsystem, or similar type programs preferably configured to input and/or receive and store the patient identification information and critical health care information of patient 14 at point of injury 16 and the added health care information provided by medical personnel from or at point of injury 16 and during one or more encounters with the medical personnel or to a time patient 14 reaches a clinical care facility.

End user computing device 26 may communicate with wearable subsystem 12 by conventional wireless technology without using cables or wires. In other examples, e.g., when conventional long-distance wireless communication is not available or at other times, end user computing device 26 may communicate with wearable subsystem 12 using short-range communication, e.g., near-field communication (NFC) or similar type near-field communication subsystem which may employ inductive coupling, optical coupling, acoustic coupling, radio-frequency coupling, or similar type coupling methods. Preferably, the near field communication employs industry-standard coupling and communications protocols. Such a design provides the ability for wearable subsystem 12 to efficiently operate regardless of the state of long distance communication. Preferably NFC can transfer data in any digital format, preferably a digital format that is self-delimited (e.g., includes headers, trailers, and other structures to avoid reading a partial data set) that can be read by computer subsystem, smart device, or similar type device and imported to an Electronic Medical Record or more generally, an Electronic Health Record (EHR), e.g., EHR 44, discussed below. Preferably the health care information regarding the care provided to patient 14 stored on wearable or PATCH subsystem 12 and the patient identifying information and critical health information can be accessed by the same medical personnel at the point of injury 16 and during one or more encounters with medical personnel using end user computing device 16. The health care information regarding the care provided to patient 14 stored to wearable or PATCH subsystem 12 as well as the patient identifying information and critical health information can be also be easily accessed by the next medical personnel caring for the patient, e.g., basic primary care 20 using end user computing device 26. Thus, the health care information regarding the care provided to patient 14 and the patient identifying information and critical health information stored on wearable or PATCH subsystem 12 follows patient 14 from point of injury 16, during one or more encounters with medical personnel, or to a time patient 14 reaches a clinical care facility. In one example, once patient 14 reaches the clinical care facility, wearable subsystem 12 preferably transfers via wireless communication the patient identification information and critical care healthcare information and the healthcare information added by medical personnel during one or more encounters with medical personnel to EHR 44 associated with a computer subsystem or an electronic storage device of the clinical care facility. In one example, system 10 may utilize reader 88, e.g., a dongle or similar type device, that may wirelessly transfer health care information provided to patient 14 by medical personnel and the patient identification information and critical healthcare information from wearable subsystem 12 to EHR 44 associated with a computer subsystem at the clinical care facility.

Figure 2:
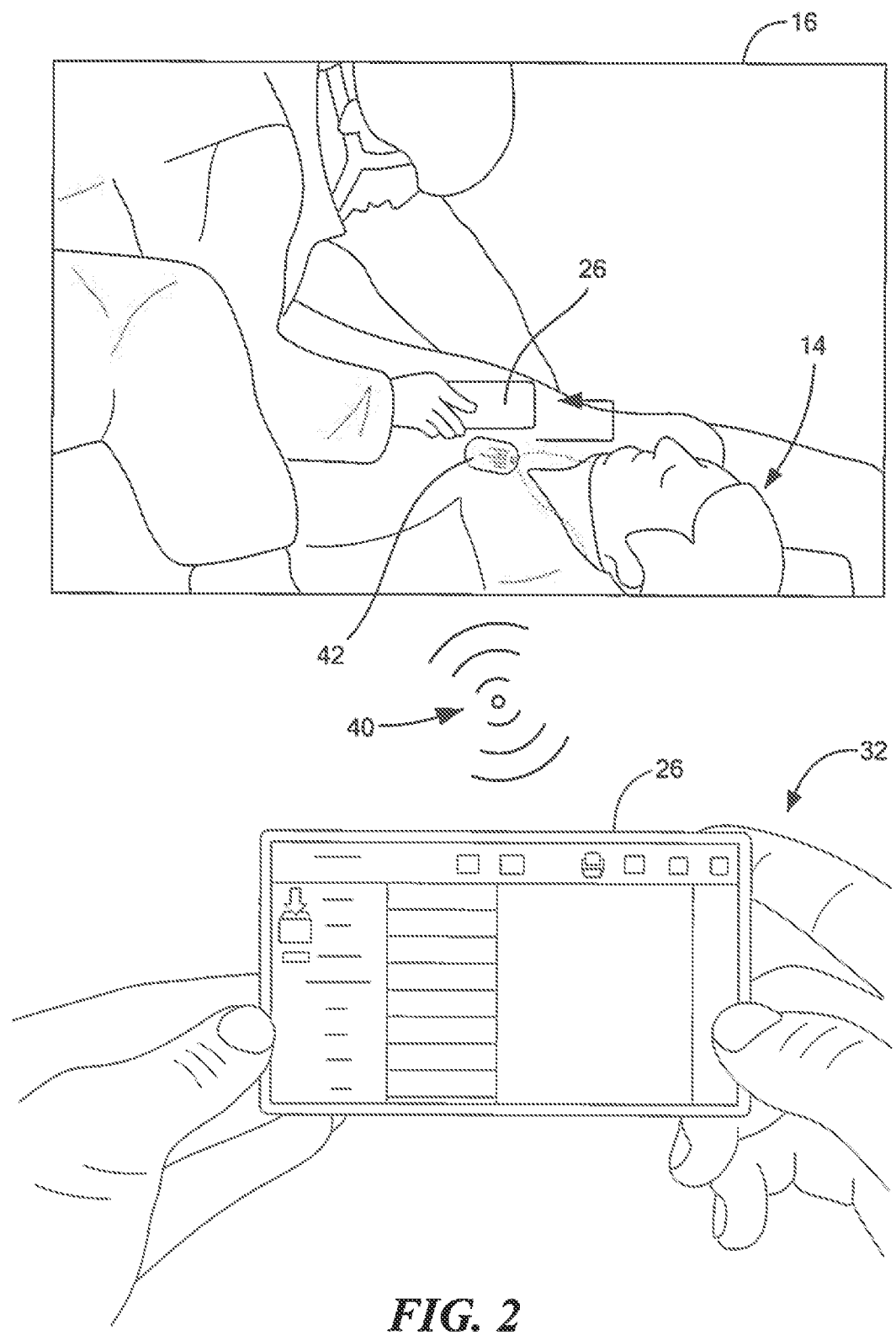
FIG. 2 is a schematic block diagram showing an example of the end user computing device shown in FIG. 1 capturing patient identification information and critical healthcare information from an electronic personal identification device located on a patient.

In one example, end user computing device 26 preferably captures via wireless communication the patient identification information and the critical health care information of patient 14 at point of injury 16 from electronic personal identification device 42, FIG. 2, e.g., an electronic medical bracelet, an electronic dog tag, an electronic dog tag silencer, an electronic medical necklace, an NFC device, or similar type device already located on a patient 14 at a point of injury 16. In this example, new patient 14 is preferably first added to the one or more casualty care programs residing in end user computing device 26, indicated at 32, and the patient identification information and the critical health care information is preferably captured by end user computing device 26 using wireless communication, indicated at 40, from electronic personal identification device 42. In one design, end user computing device 26 may communicate with electronic personal identification device 42 by conventional wireless technology without using cables or wires. In other examples, e.g., when conventional long distance wireless communication is not available or at other times, end user computing device 26 may communicate with electronic personal identification device 42 using short range communication, e.g., NFC or other similar short range communication system and methods, such as Ultra-wideband, Bluetooth, and the like, which can both be preferably enabled by a NFC connection. Preferably the NFC device activates when end user computing device 26 is brought near electronic personal identification device 42 and transfers information necessary to automatically initiate another short range communication connection using a communications subsystem which may preferably have the ability to transfer larger quantities of information at faster speeds. In one example, the patient identifying information and critical health information stored on personal electronic storage device 42 may be transmitted to end user computing device 16 via NFC by touching (or bringing very near) end user computing device 16 to personal electronic storage device 42, in this example, no long distance wireless communication, e.g., LTE, 3G, 4G, 5G, and the like, is required. The patient identifying information and critical health information stored on personal electronic storage device 42 preferably automatically populates the one or more of the casualty care programs or apps located on end user computing device 26 and additional information may be added as needed.

Figure 3:
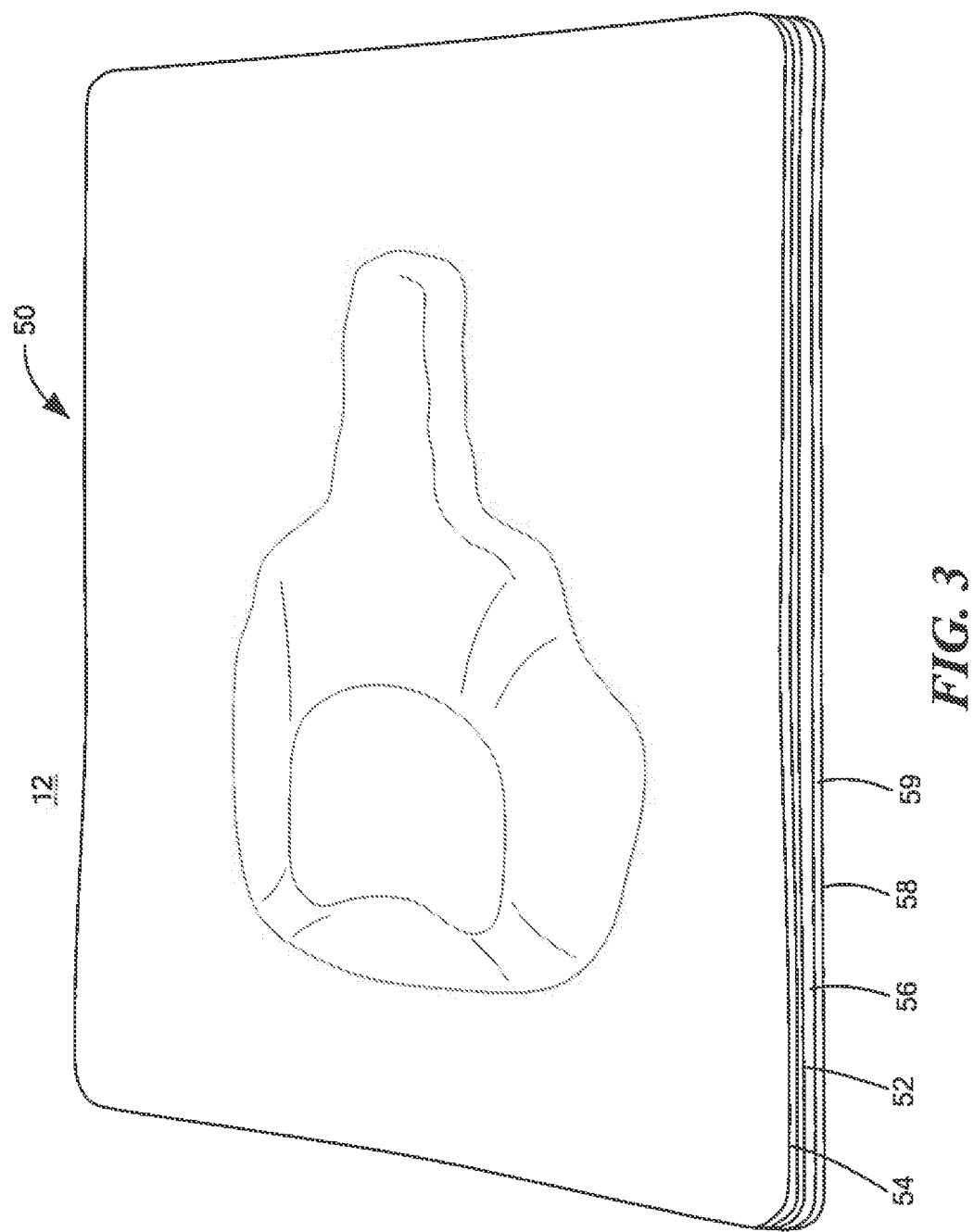
FIG. 3 is a schematic diagram showing an example of the wearable subsystem shown in FIG. 1 configured as an adhesive patch.

In one design, wearable subsystem 12 FIG. 1, may be configured as an adhesive patch which easily attaches to skin 60 of patient 14. FIG. 3 shows one example of wearable subsystem 12 configured as adhesive patch 50. Adhesive patch 50 preferably includes flexible printed circuit board 52, shown in greater detail in FIG. 4. Flexible printed circuit board 52 preferably includes one or more processing subsystems 62, electronic storage device 64, firmware, NFC Transceiver 100 and power supply 66 with connected power source 67. Processing subsystem 62 may include one or more processors, an application-specific integrated circuit (ASIC), firmware, hardware, and/or software (including firmware, resident software, micro-code, and the like) or a combination of both hardware and programs that may all generally be referred to herein as a "processing subsystem", which may be part of system 10 and method thereof. Electronic storage device 64 may include any combination of computer-readable media or memory. The computer-readable media or memory may be a computer-readable signal medium or a computer-readable storage medium. The computer-readable storage medium or memory may be electronic, magnetic, optical, electromagnetic, infrared, a semiconductor subsystem, apparatus, or device, or any suitable combination of the foregoing. Other examples of electronic storage device 64 may include an electrical connection having one or more wires, random access memory (RAM), read-only memory (ROM), erasable programmable read-only memory (EPROM or Flash memory), an optical fiber, an optical storage device, a magnetic storage device, or any suitable combination of the foregoing. As disclosed herein, electronic storage device 64 may be any tangible medium that can contain, or store one or more programs for use by or in connection with one or more processors on flexible printed circuit board 52. Processing subsystem 62, electronic storage device 64, and NEC transceiver 100 may be implemented in a single ASIC or as a combination of integrated circuits each implementing one of more or the subsystem functions.

Computer program code for the one or more programs for carrying out the instructions or operation of one or more embodiments wearable subsystem 12 may be written in any combination of one or more programming languages, including an object oriented programming language, e.g., C++, Smalltalk, Java, and the like, and conventional procedural programming languages, such as the "C" programming language, Assembly language or similar programming languages.

One of more embodiments of wearable subsystem 12 of system 10 and the method thereof disclosed below with reference to flowchart illustrations and/or block diagrams of systems and methods are possible. Each block of the flowchart illustrations and/or block diagrams, and combinations thereof may be implemented by computer program instructions. These computer program instructions may be provided to the processing subsystem or other programmable data processing apparatus to produce a machine, such that the instructions, which execute by the processing subsystem create means for implementing the functions/acts specified in the flowchart and/or block diagram block or blocks.

Figure 5A:
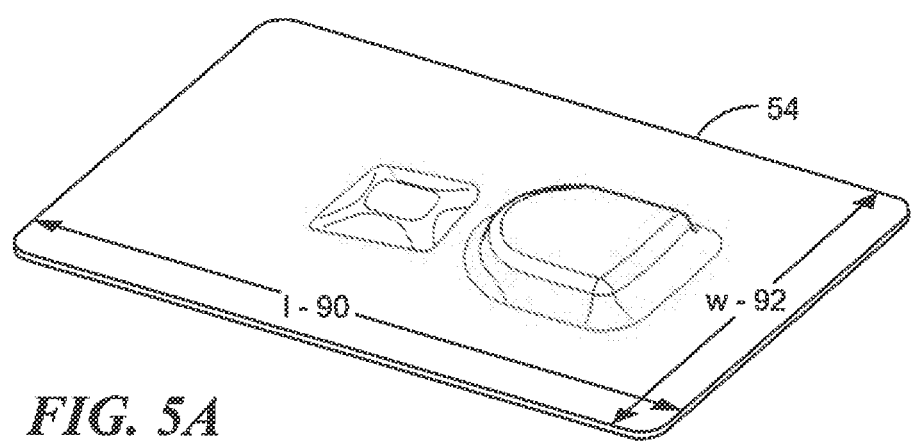
FIGS. 5A and 5B are schematic block diagrams showing in further detail the one example of the structure of the plurality of flexible layers of the adhesive patch shown in FIG. 3.
Figure 5B:
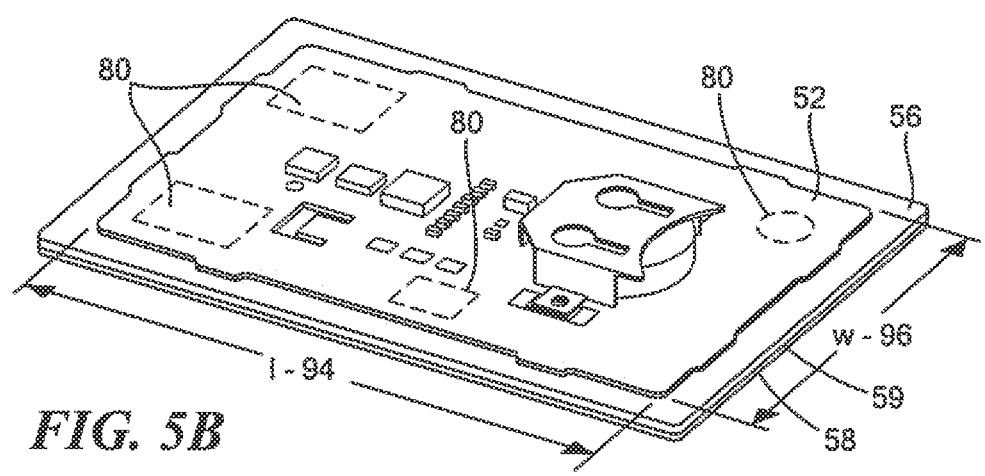

Adhesive patch 50, FIG. 3, preferably includes a plurality of flexible layers 54, 56 about flexible printed circuit board 52 which preferably sandwich flexible printed circuit board 52 as shown. FIG. 5A shows in further detail top one example of the structure of flexible top layer 54. FIG. 5B shows in further detail one example of the structure of flexible bottom layer 56 and flexible printed circuit board 52 disposed thereon.

Figure 5C:
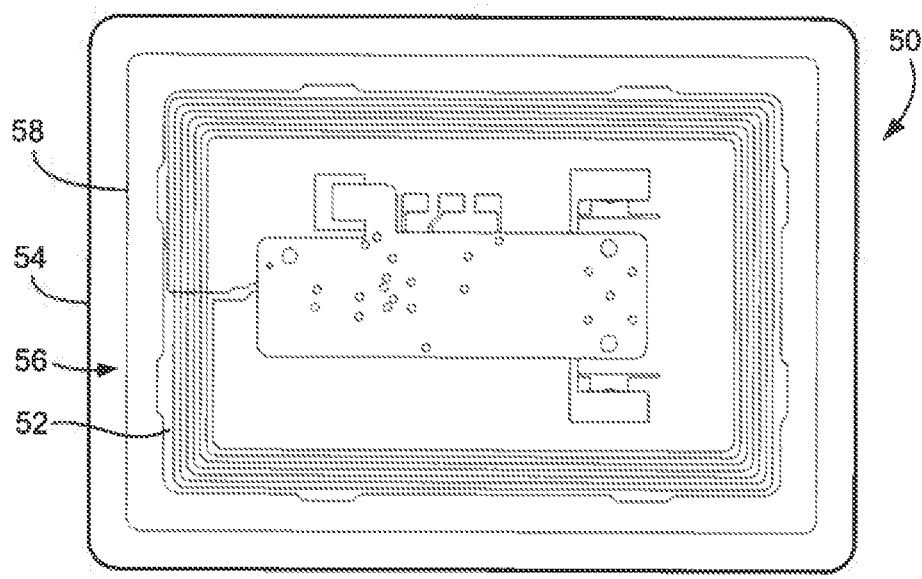
FIG. 5C is a bottom view of the adhesive patch shown in FIGS. 5A and 5B when the bottom adhesive layer shown in FIG. 5B is transparent.

Adhesive patch 50 of wearable subsystem 12, as in caption 18, preferably attaches to skin 60, FIG. 1, of patient 14 at point of injury 16 and remains attached to patient 14 from point of injury 16 and during one or more encounters of patient 14 with medical personal or to a time patient 14 reaches a clinical care facility. In one example, adhesive patch 50 preferably includes adhesive cover layer 58, FIGS. 3 and 5B with adhesive 59 disposed thereon such that adhesive cover layer 58 may be peeled off to expose adhesive 59 which attaches adhesive patch 50 to skin 60, FIG. 1, of patient 14. In one example the adhesive provided by adhesive 59 of adhesive cover layer 58, FIGS. 3 and 5B, may be e.g., FLX054516 2378SL DLC-503-PT (FLEXcon®, Spencer, Mass.). FIG. 5C is a bottom view of adhesive patch 50 shown in FIGS. 5A and 5B showing in further detail adhesive cover layer 58 which may be peeled off to expose adhesive 59 such that adhesive patch 50 of one embodiment of wearable subsystem 12 may be attached to skin 60, FIG. 1, of patient 14. In FIG. 5C adhesive cover layer 58 and adhesive 59 are shown as transparent so that the bottom side of flexible printed circuit board 52 is visible.

Figure 6:
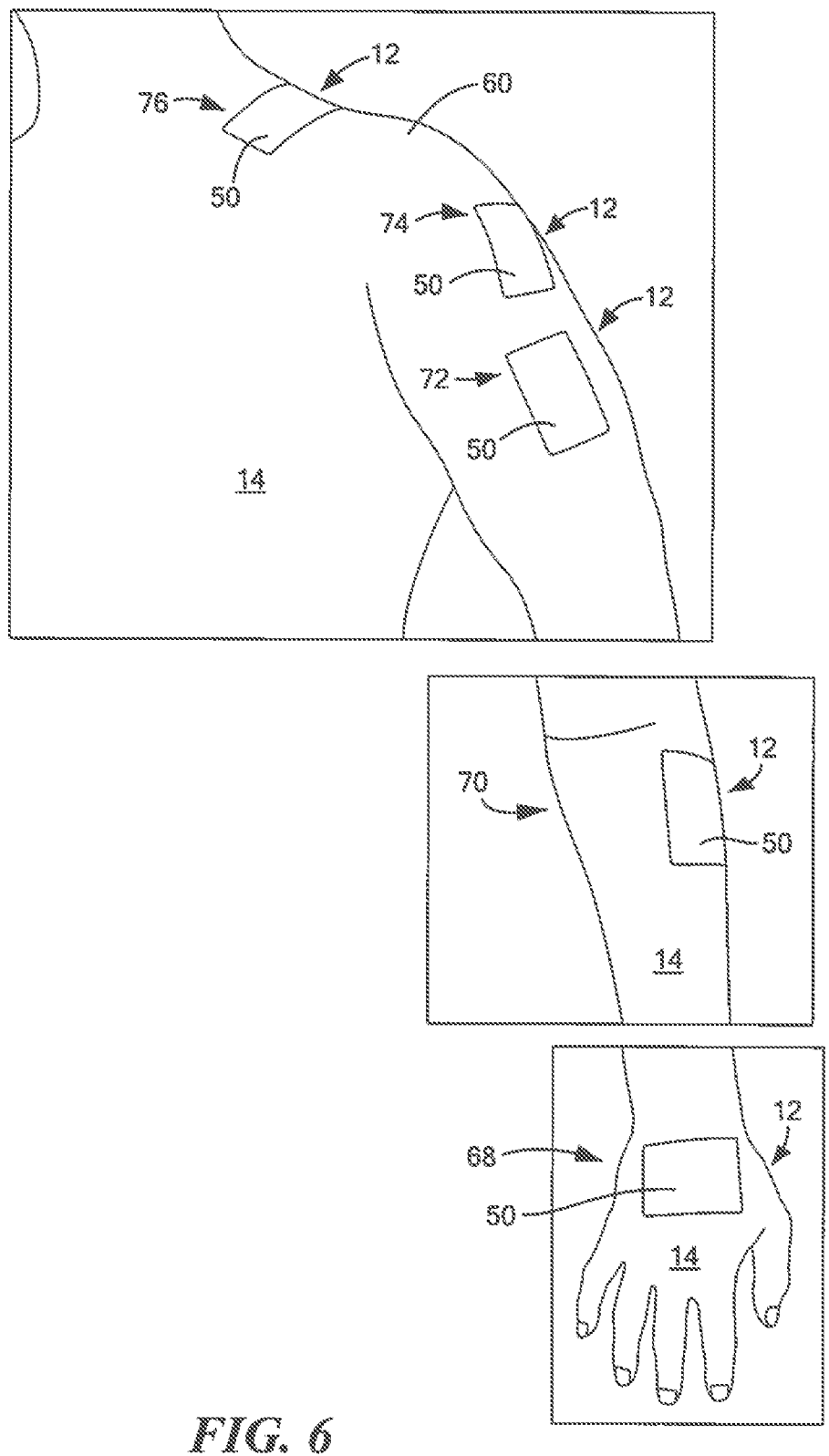
FIG. 6 shows examples of the wearable patch subsystem shown in one or more of FIGS. 1-5 located on easily accessible areas of the patient.

FIG. 6 shows in further detail examples of adhesive patch 50 of wearable subsystem 12 which is preferably attached to an easily accessible area of patient 14, e.g., the back of the hand, indicated at 68, the forearm, indicated at 70, the bicep, indicated at 72, the deltoid, indicated at 74, the clavicle, indicated at 74, or any other easily accessible area of patient 14.

In one design, one or more or both of flexible layers 54, 56, FIGS. 3, 5A, and 5B, may be configured to increase moisture vapor transmission rate from the skin of the patient to provide for increased breathability and/or attachability of adhesive patch 50 of wearable subsystem 12 to the skin of the patient. In one example, flexible top layer 54 may be made of Derma Flex P.E.F. 32 white H-566 90 foam and flexible bottom layer 56 may be made of FLX054516 2378SL DLC-503-PT, e.g., available from FLEXcon, Spencer, Mass., which each may preferably increase moisture vapor transmission rate from the skin of the patient to provide for increased breathability and attachability of adhesive patch 50 to the skin of patient 14. In another example, flexible printed circuit board 52, FIG. 5B, may include one or more openings, e.g., openings 80, which preferably increase the moisture vapor transmission rate from the skin of the patient to provide for increased breathability of adhesive patch 50. In yet another example, flexible printed circuit board 52 may include a breathable substrate configured increase the moisture vapor transmission rate from the skin of the patient to provide for increased breathability of adhesive patch 50.

Wearable subsystem 12 and adhesive patch 50 shown in one or more of FIGS. 1-6 preferably has a small area, e.g., less than about 35 cm$^2$. One example of a prototype of wearable subsystem 12 configured as adhesive patch 50 includes flexible layer 54, FIG. 5A, having a length, l-90, of about 635 cm and a width, w-92 of about 4.6 cm and flexible layer 56, FIG. 5B, having a length, l-94, of about 5.10 cm and a width, w-96 of about 3.30 cm.

Figure 4:
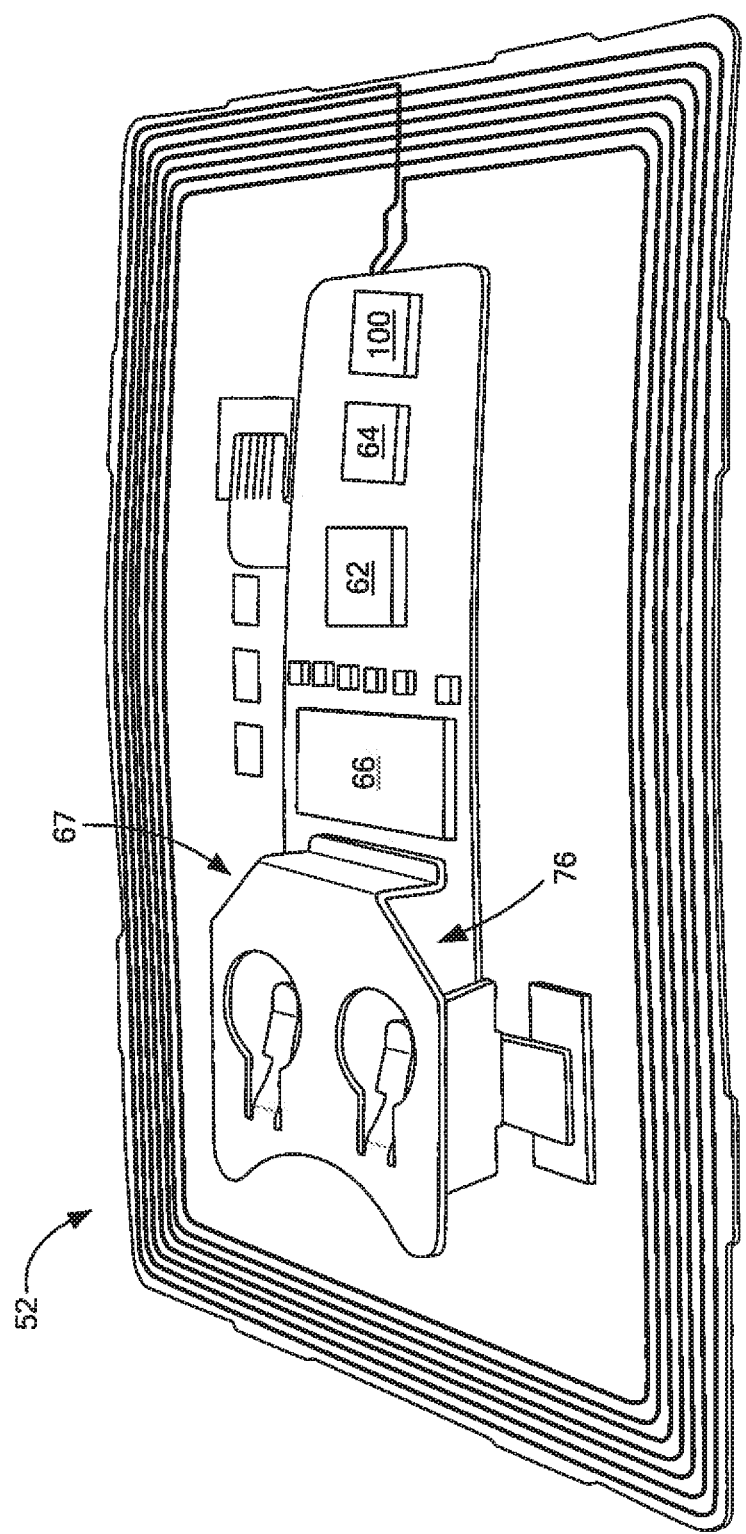
FIG. 4 is a schematic diagram showing in further detail the flexible printed circuit board shown in FIG. 3.
Figure 7:
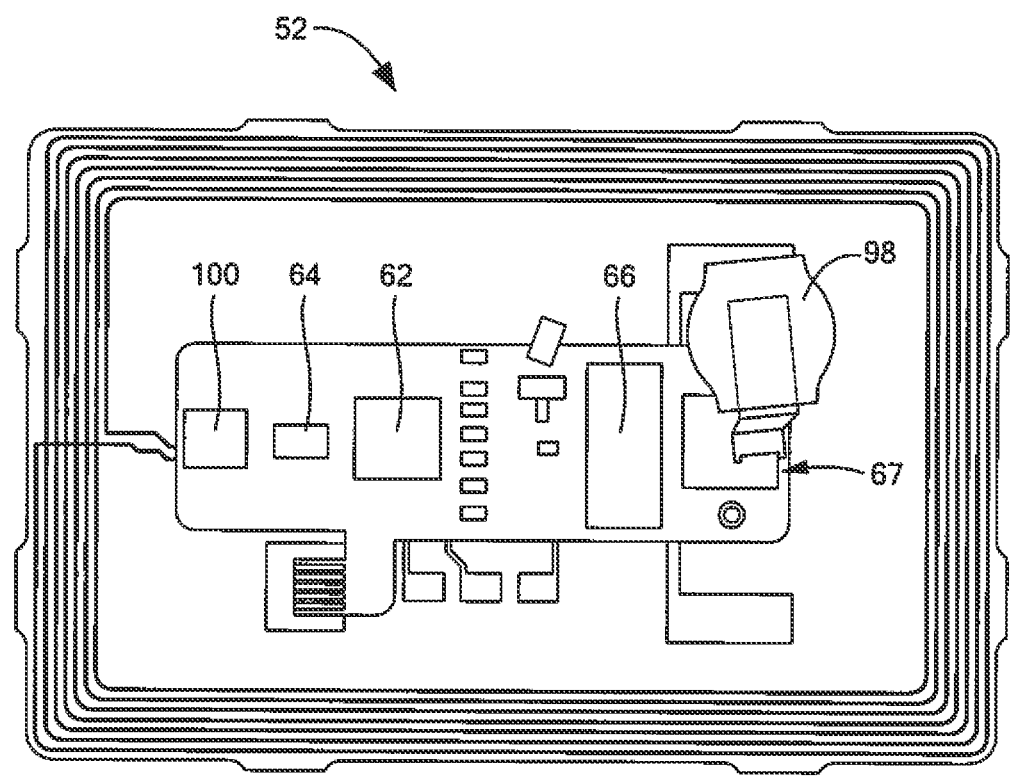
FIG. 7 is a schematic diagram showing an example of the flexible printed circuit board shown in one or more of FIGS. 3-5 using a supercapacitor as the power source for the power supply.

In one design, power supply 66, FIG. 4, is preferably configured as power conditioning circuitry or subsystem on flexible printed circuit board 52 and may use a small sized battery, e.g., a CR1225 battery (Exell Battery, North Las Vegas, Nev.) for power source 67, which in this example may be inserted into battery holder 76 and preferably provides power to wearable subsystem 12 for an extended period of time, e.g., about 3,200 hours, or similar extended period of time. In another design, power supply 66 may use a supercapacitor, e.g., supercapacitor 98. FIG. 7, for power source 67, which preferably provides power to system 10 for an extended period of time, e.g. about 2,000 hours or similar extended period of time.

Figure 8:
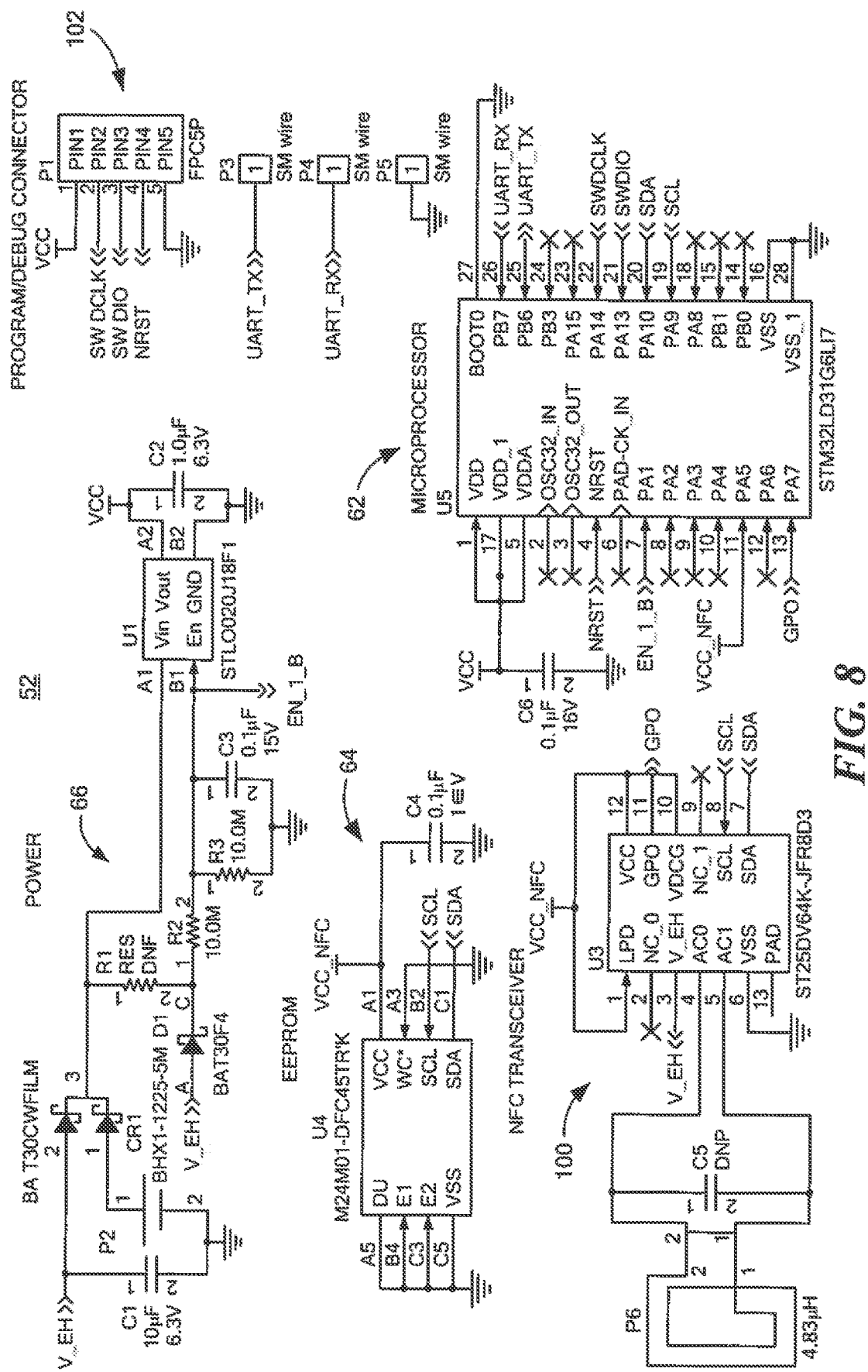
FIG. 8 is a circuit diagram showing in further detail the primary components of the wearable subsystem shown in one or more of FIGS. 1-7.

FIG. 8 is a circuit diagram showing in further detail one example of the primary components of flexible printed circuit board 52 of wearable subsystem 12 and adhesive patch 50 shown in one or more of FIGS. 1-7 including, inter alia, processing subsystem 62, electronic storage device 64, power supply 66, and also showing an example of NFC transceiver 100, and connector 102.

Figure 9:
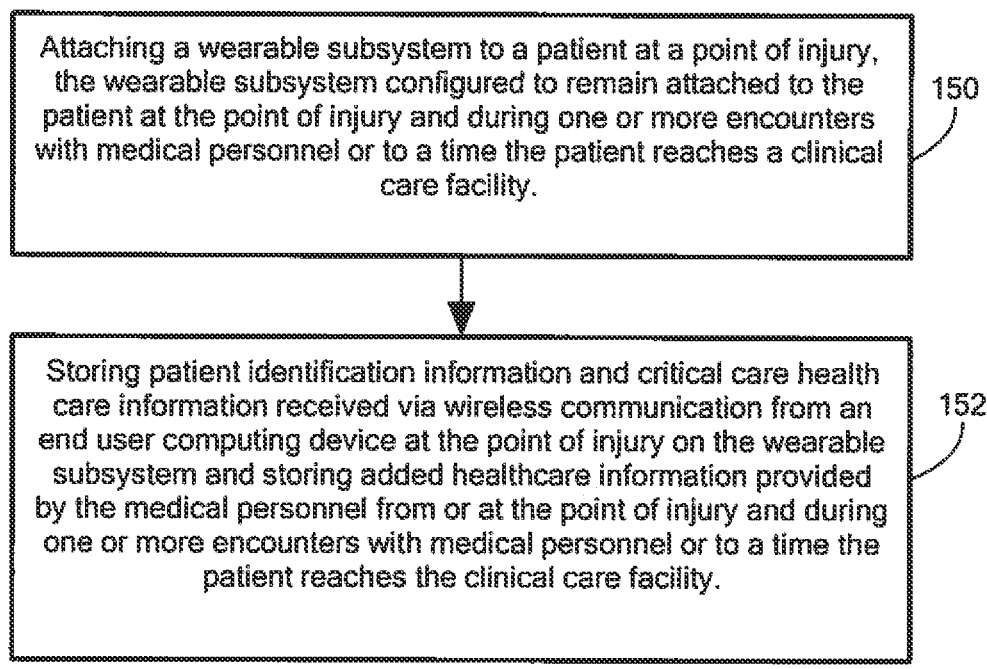
FIG. 9 is a block diagram showing one example of the primary steps of one example of the method for electronically coordinating and documenting patient care regardless of physical setting.

One example of the method for electronically coordinating and documenting patient care regardless of physical setting includes attaching a wearable subsystem to a patient at a point of injury, the wearable subsystem configured to remain attached to the patient at the point of injury and during one or more encounters with medical personnel or to a time the patient reaches a clinical care facility, step 150, FIG. 9. The method also includes storing patient identification information and critical care health care information received via wireless communication from an end user computing device at the point of injury on the wearable subsystem and storing added healthcare information provided by the medical personnel from or at the point of injury and during one or more encounters with medical personnel or to a time the patient reaches the clinical care facility, step 152.

The result is wearable subsystem 12 of system 10 and the method thereof for electronically coordinating and documenting patient care regardless of physical setting is preferably easily maintained through multiple patient handoffs to various medical personnel and efficiently and effectively stores patient identification information and critical health care information and health care information provided by medical personnel from or at the point of injury and during one or more encounters by medical personnel or to a time the patient reaches a clinical care facility. Because wearable subsystem 12 may be configured as an adhesive patch, it can be easily attached to the patient 14 and requires little training to use. The unique structure of wearable subsystem configured as an adhesive patch provides for increased moisture vapor transmission which increases the breathability and/or attachability of the adhesive patch. The wearable subsystem preferably has a small area and can easily be placed on any exposed area of the skin of the patient away from the injury.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the art and are within the following claims.

What is claimed is:

1. A system to electronically coordinate and document patient care regardless of physical setting, the system comprising:
a wearable subsystem attached to a patient at the point of injury and configured to remain attached to the patient at the point of injury and during one or more encounters with medical personnel or to a time the patient reaches a clinical health care facility, the wearable subsystem configured to store patient identification information and critical health care information added by medical personnel via an end user computing device and transfer the patient identification information and critical health care information to the wearable subsystem via direct rapid two-way wireless communication between an end user computing device and the wearable patch subsystem at the point of injury and configured to store added health care information provided by medical personnel via an end user computing device and transfer the added health care information provided by medical personnel via direct rapid two-way wireless communication between an end user computing device and the wearable patch subsystem from or at the point of injury and during the one or more encounters with the medical personnel or to a time the patient reaches a clinical care facility.

2. The system of claim 1 in which the wearable subsystem is configured as an adhesive patch.

3. The system of claim 2 in which the adhesive patch includes a flexible printed circuit board.

4. The system of claim 3 in which the flexible printed circuit board includes one or more of: a processing subsystem, an electronic storage device, firmware, and a power supply.

5. The system of claim 3 in which the adhesive patch includes a plurality of flexible layers about the flexible printed board.

6. The system of claim 5 in which one of the plurality of flexible layers includes an adhesive layer configured to attach to the skin of the patient.

7. The system of claim 6 in which one or more of the plurality of flexible layers are configured to increase moisture vapor transmission rate of vapor from skin of the patient to provide increased breathability and attachability of the adhesive patch subsystem to the skin.

8. The system of claim 3 in which flexible printed circuit board includes a breathable substrate configured to increase moisture vapor transmission rate of vapor from skin of the patient to provide increased breathability.

9. The system of claim 3 in which the flexible printed circuit board includes a plurality of openings configured to increase moisture vapor transmission rate of vapor from skin of the patient to provide increased breathability.

10. The system of claim 1 in which the wearable subsystem has a small area.

11. The system of claim 10 in which the small area is less than about 35 cm$^2$.

12. The system of claim 4 in which the power supply includes a battery configured to provide power for an extended period of time.

13. The system of claim 4 in which the power supply includes a supercapacitor configured to provide power for an extended period of time.

14. The system of claim 2 in which the wearable subsystem is attached to an easily accessible area of the patient.

15. The system of claim 1 in which the wearable subsystem is configured to transfer the patient identification information and critical health care information and the health care information added by the medical personnel to an electronic medical record or electronic health record.

16. The system of claim 1 in which the wearable subsystem is configured to operate regardless of a state of long distance communication.

17. The system of claim 16 in which wearable subsystem is configured to operate using short range communication.

18. The system of claim 1 in which the end user computing device is configured to capture via wireless communication the patient identification information and the critical health care information from an electronic personal identification device already located on a patient at a point of injury.

19. The system of claim 18 in which the end user computing device operates using short range communication.

20. The system of claim 18 in which the end user computing device includes one or more casualty care programs configured to input and/or receive and store the patient identification information and critical health care information and the health care information provided by the medical personnel.

21. The system of claim 20 in which the one or more casualty care programs include an electronic Tactical Combat Casualty Care Program (TCCC).

22. The system of claim 21 in which the one or more casualty care programs include an electronic Patient Care Reporting (ePCR) subsystem.

23. A method for electronically coordinating and documenting patient care regardless of physical setting, the method comprising:
   attaching a wearable subsystem to a patient at a point of injury, the wearable subsystem configured to remain attached to the patient at the point of injury and during one or more encounters with medical personnel or to a time the patient reaches a clinical care facility; and
   storing patient identification information and critical care health care information added by medical personnel via an end user computing device and transfer the patient identification information and critical health care information to the wearable subsystem via direct rapid two-way wireless communication between an end user computing device and the wearable patch subsystem at the point of injury and storing added healthcare information provided by the medical personnel via an end user computing device and transfer the added health care information provided by medical personnel via direct rapid two-way wireless communication between an end user computing device and the wearable patch subsystem from or at the point of injury and during one or more encounters with medical personnel or to a time the patient reaches the clinical care facility.

24. The method of claim 23 in which wireless communication includes short range communication.

25. The method of claim 23 further including transferring the patient identification information and critical health care information and health care added by medical personnel to an electronic medical record or electronic health record.

26. The method of claim 23 further including increasing moisture transmission rate of the wearable subsystem to provide increased breathability and attachability of the wearable subsystem to the patient.

27. The method of claim 23 further including capturing via wireless communication the patient identification information and critical health care information from an electronic personal communication device already located on the patient at the point of injury.

28. The method of claim 27 further including capturing via the patient identification information and critical health care information from an electronic personal communication device already located on the patient at the point of injury using short range communication.

* * * * *